A61B 2017/00424;

United States Patent
Melsheimer et al.

(10) Patent No.: US 11,883,042 B2
(45) Date of Patent: Jan. 30, 2024

(54) MEDICAL DEVICE FOR STONE MANAGEMENT

(71) Applicant: Cook Medical Technologies LLC, Bloomington, IN (US)

(72) Inventors: Jeffry S. Melsheimer, Springville, IN (US); Donald Sandmore, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 55 days.

(21) Appl. No.: 17/520,838

(22) Filed: Nov. 8, 2021

(65) Prior Publication Data

US 2022/0142659 A1 May 12, 2022

Related U.S. Application Data

(60) Provisional application No. 63/112,283, filed on Nov. 11, 2020.

(51) Int. Cl.
*A61B 17/22* (2006.01)
*A61M 25/00* (2006.01)
*A61B 17/00* (2006.01)

(52) U.S. Cl.
CPC ...... *A61B 17/22* (2013.01); *A61B 2017/0042* (2013.01); *A61B 2017/00367* (2013.01);
(Continued)

(58) Field of Classification Search
CPC .......... A61B 17/22; A61B 2017/00367; A61B 2017/0042; A61B 2017/00424;
(Continued)

(56) References Cited

U.S. PATENT DOCUMENTS 5,254,117 A * 10/1993 Rigby ................... A61M 1/774
606/49
5,273,524 A * 12/1993 Fox ..................... A61M 1/7415
606/45
(Continued)

OTHER PUBLICATIONS

Cook Medical, "LithAssist® Suction Control for Laser Lithotripsy," product brochure, https://www.cookmedical.com/products/e91c555a-69af-4fe5-8aae-50dd906b9726/ (4 pp.).
(Continued)

*Primary Examiner* — Jocelin C Tanner
(74) *Attorney, Agent, or Firm* — Crowell & Moring LLP

(57) ABSTRACT

A medical device for stone management comprises a catheter comprising a proximal end, a distal end, and a first lumen and a second lumen disposed therethrough. A handle assembly is interconnected with the proximal end of the catheter, the handle assembly comprising a body defining an interior cavity, a first section and a second section. An interior passageway is disposed within the interior cavity and in fluid communication with the first lumen of the catheter. A valve assembly interconnected with the interior passageway. An actuator assembly is engaged with the valve assembly, the actuator having a first position and a second position. A vacuum port is in communication with the interior passageway and positioned on the second section of the handle. The second section of the handle forms an angle with respect to the first section of the handle.

20 Claims, 9 Drawing Sheets

(52) U.S. Cl.
CPC ........... *A61B 2017/22079* (2013.01); *A61B 2217/005* (2013.01); *A61M 2025/0039* (2013.01)

(58) Field of Classification Search
CPC ... A61B 2017/22079; A61B 2217/005; A61M 25/0026; A61M 25/0097; A61M 39/22; A61M 2025/0031; A61M 2025/0039
See application file for complete search history.

(56) References Cited

U.S. PATENT DOCUMENTS

| | | | |
|---|---|---|---|
| 5,312,332 A * | 5/1994 | Bales | A61B 17/00234 604/28 |
| 5,520,634 A * | 5/1996 | Fox | A61B 17/32002 606/180 |
| 5,868,785 A | 2/1999 | Tal et al. | |
| 6,918,902 B2 | 7/2005 | French et al. | |
| 7,025,755 B2 | 4/2006 | Epstein | |
| 7,811,256 B2 * | 10/2010 | Landman | A61M 1/774 604/131 |
| 7,967,774 B2 | 6/2011 | Bayat | |
| 10,420,579 B2 | 9/2019 | Wiener et al. | |
| 10,478,211 B2 | 11/2019 | Stulen et al. | |
| 2005/0256446 A1 | 11/2005 | Criscuolo et al. | |
| 2009/0157002 A1 * | 6/2009 | Dumot | A61M 25/007 604/523 |
| 2017/0105746 A1 | 4/2017 | O'Keefe et al. | |
| 2018/0317948 A1 | 11/2018 | Suh et al. | |

OTHER PUBLICATIONS

Cook Medical, "Take Control,"LithAssist® Suction Control for Laser Lithotripsy, product brochure (4 pp.).

Dauw et al., "A Usability Comparison of Laser Suction Handpieces for Percutaneous Nephrolithotomy," Journal of Endourology, vol. 30, No. 11, Nov. 2016, Mary Ann Liebert, Inc., pp. 1165-1168, DOI: 10.1089/end.2016.0203 (4 pp.).

Du, Chuance et al, "A study on the clinical application of a patented perfusion and suctioning platform and ureteral access sheath in the treatment of large ureteral stones below L4 level,"International Urology and Nephrology (2019) 51:207-213, DOI: 10.1007/s 11255-018-2049-9 (7 pp.).

Hoffman et al., "Percutaneous Renal Stone Extraction: In Vitro Study of Retrieval Devices," Journal of Endourology, vol. 32, No. 12, Dec. 2018, $^{ul;1aul;0}$Mary Ann Liebert, Inc., pp. 1154-1159, DOI: 10.1089/end 20180565 3 pp.).

Li et al., "A Novel Semirigid Ureterorenoscope with Vacuum Suctioning System for Management of Single Proximal Ureteral and Renal Pelvic Stones: An Initial Experience," 0022-5347/04/1722-0559/0 vol. 172, 559-561, Aug. 2004, The Journal of Urology® Printed in U.S.A., Copyright © 2004 by American Urological Association, DOI: 10.1097/01.ju.0000129195.71871.17 (6 pp.).

Pugh, Joseph W. et al., "New Instrumentation in Percutaneous Nephrolithotomy," Indian J Urol. Jul.-Sep. 2010; 26(3): 389-394, doi: 10.4103/0970-1591.70579, PMCID: PMC2978441, PMID: 21116361 (6 pp.).

* cited by examiner

US 11,883,042 B2

MEDICAL DEVICE FOR STONE MANAGEMENT

RELATED APPLICATIONS

This application claims the benefit of U.S. Provisional Application No. 63/112,283, filed Nov. 11, 2020, which is incorporated by reference herein in its entirety.

BACKGROUND

1. Technical Field

The present disclosure relates generally to the field of medical devices, and more particularly, the disclosure relates to medical devices, methods and kits useful in the disruption and removal of unwanted materials, such as calculi and other formations, from within body lumens.

2. Background Information

There is a continuing need for instruments to diagnose and treat people by means of minimally-invasive surgical procedures. For example, various organs and passages in the body are subject to the development of stones, calculi and the like. Kidney stones are a common problem in the United States. Kidney stones are painful and are the most frequent cause of kidney inflammation. Calculi and concretions in other parts of the biliary system are also commonplace. Similarly, stones, calculi, concretions and the like can develop throughout the renal or urinary system, not only in the ureters and distal to them, but also in the renal tubules and in the major and minor renal calyxes.

Minimally invasive surgical procedures have been developed for the removal of stones, calculi, concretions and the like from the biliary, vascular, and urinary systems, as well as for the removal or retrieval of foreign bodies from a variety of locations in the body. Such procedures avoid the performance of open surgical procedures such as, for example, an anatrophic nephrolithotomy.

Minimally invasive procedures can instead employ percutaneous access, in which stones, calculi, concretions, foreign bodies and the like are removed through a percutaneously inserted access sheath. Several access routes are suitable, depending upon the specific system and the particular location in the system at which the stones, calculi, concretions, foreign bodies or the like are found. It is sometimes necessary, or otherwise desirable, to remove unwanted materials disposed within a bodily passage. For example, lithotripsy—the disruption and removal of calculi, or stones, from a region of the body—is frequently performed to remove stones disposed in a salivary duct or the urinary tract. Various types of lithotripsy are known, including shockwave lithotripsy, extracorporeal shockwave lithotripsy, laser lithotripsy, percutaneous lithotripsy, endoscopic lithotripsy, and pneumatic lithotripsy.

An exemplary method of performing lithotripsy on a stone disposed in a bodily passage comprises the steps of: inserting a sheath that has a first proximal end, a first distal end, and that defines a first lumen into the bodily passage such that the first distal end is disposed in the bodily passage; inserting a scope that has a second proximal end, a second distal end, and that defines a second lumen through the first lumen such that the second distal end is disposed distal to the first distal end of the sheath; inserting a lithotripter comprising a firing handle and a probe having a third proximal end and a third distal end through the second lumen such that the third distal end is disposed distal to the second distal end of the scope; navigating the third distal end of the probe towards the stone; contacting the third distal end of the probe with the stone; and activating the firing handle of the lithotripter to fragment the stone. In such procedures, an apparatus may be used to apply suction to remove the fragments of the stone from the body cavity of the patient.

It would be highly desirable to have a device suitable for use during lithotripsy procedures and provides ease of removal of fragments from the body of a patient. It would further be highly desirable to provide a device to provide the user with increased control the flow of suction while performing lithotripsy.

BRIEF SUMMARY

Various exemplary medical devices and methods are described and illustrated herein.

In one aspect, a medical device for stone management comprises a catheter comprising a proximal end, a distal end, and a first lumen and a second lumen disposed therethrough. A handle assembly is interconnected with the proximal end of the catheter, the handle assembly comprising a body defining an interior cavity, a first section and a second section. An interior passageway is disposed within the interior cavity and in fluid communication with the first lumen of the catheter; the interior passageway having an angled configuration with respect to the catheter and having a first end and a second end. A valve assembly interconnected with the interior passageway. An actuator assembly is engaged with the valve assembly, the actuator having a first position and a second position. A vacuum port is in communication with the interior passageway and positioned on the second section of the handle. The second section of the handle forms an angle with respect to the first section of the handle. In one embodiment, the actuator includes a moveable arm pivotably connected to the second section of the handle assembly. In another embodiment, the second section of the handle forms an angle of less than 90 degrees with respect to the first section of the handle.

In another aspect, medical device for stone management comprises a multi-lumen catheter comprising a proximal end, a distal end, and an inner lumen and an outer lumen at least partially surrounding the first lumen. A handle assembly is interconnected with the proximal end of the catheter, the handle assembly comprising a body defining an interior cavity, a first section and a second section. An interior passageway is disposed within the interior cavity and positioned in the second section of the handle assembly of the handle assembly; the interior passageway in fluid communication with the outer lumen of the catheter and having a first end and a second end. A valve assembly is interconnected with the interior passageway and positioned within the second section of the handle. An actuator assembly is engaged with the valve assembly, the actuator having a first position and a second position. A vacuum port positioned on the second section of the handle assembly and in communication with the interior passageway. The second section of the handle forms an angle with respect to the first section of the handle. In one embodiment, a hub is positioned within the interior cavity of the handle assembly, the hub comprising a first port, a second port, third port, and a central passage. In another embodiment, the handle assembly further comprises an irrigation port in communication with the third port of the hub.

In yet another aspect, a medical device for stone management comprises a multi-lumen catheter comprising a proximal end, a distal end, an inner lumen and an outer lumen at least partially surrounding the first lumen. A handle assembly is interconnected with the proximal end of the catheter, the handle assembly comprising a body defining an interior cavity, a first section and a second section. An interior passageway is disposed within the interior cavity and positioned in the second section of the handle assembly of the handle assembly; the interior passageway in fluid communication with the outer lumen of the catheter and having a first end and a second end. A hub is positioned within the interior cavity of the handle assembly and in communication with the interior passageway, the hub comprising a first port, a second port, third port, and a central passage. A valve assembly is interconnected with the interior passageway. An actuator assembly is engaged with the valve assembly, the actuator having a first position and a second position. A vacuum port is positioned on the second section of the handle assembly and in communication with the interior passageway. The second section of the handle forms an angle with respect to the first section of the handle.

DETAILED DESCRIPTION OF THE DRAWINGS AND THE PRESENTLY PREFERRED EMBODIMENTS

Figure 1:
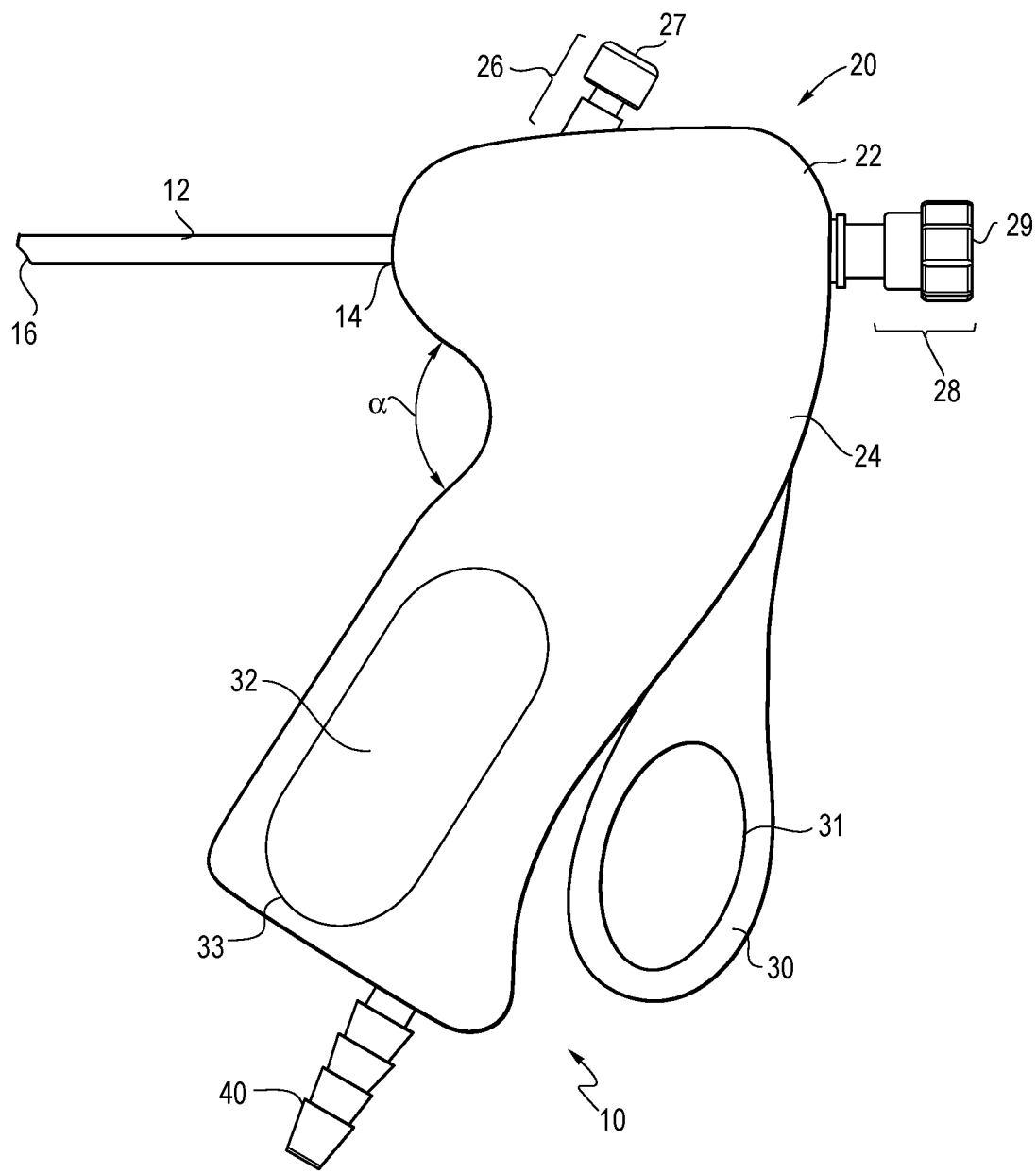
FIG. 1 illustrates an exterior view of an embodiment of a medical device for stone management.

Example embodiments are disclosed herein. It is understood, however, that the disclosed embodiments are merely exemplary and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and/or teaching one skilled in the art to practice the embodiments.

Unless defined otherwise, all technical and scientific terms used herein have the same meaning as commonly understood by one of ordinary skill in the art to which this invention pertains.

The terms "patient," "subject," and "recipient" as used in this application may refer to any animal, particularly humans.

The terms "proximal" and "distal" will be used to describe opposing axial ends of the ureteral stent, as well as the axial ends of various component features. The term "proximal" is used to refer to the end of the medical device (or component thereof) that is closest to the operator during use of the system. The term "distal" is used to refer to the end of the medical device (or component thereof) that is initially inserted into the patient, or that is closest to the patient during use.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part 1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "medical device" means any object that is itself or that includes a component that is intentionally inserted into the body of a patient as part of a medical treatment, and that comprises a structure adapted for introduction into a patient. The medical device can be a tool, such as, without limitation, a catheter, a wire guide, a forceps, or a scissors used to affect a surgical procedure at and/or deliver a second medical device to a treatment site in a patient.

The terms "about" and "substantially" are used herein with respect to measurable values and ranges due to expected variations known to those skilled in the art (e.g., limitations and variability in measurements).

The terms "at least one" and "one or more of" an element are used interchangeably and may have the same meaning. These terms, which refer to the inclusion of a single element or a plurality of the elements, may also be represented by the suffix "(s)" at the end of the element. For example, "at least one metal", "one or more metals", and "metal(s)" may be used interchangeably and are intended to have the same meaning.

Figure 2:
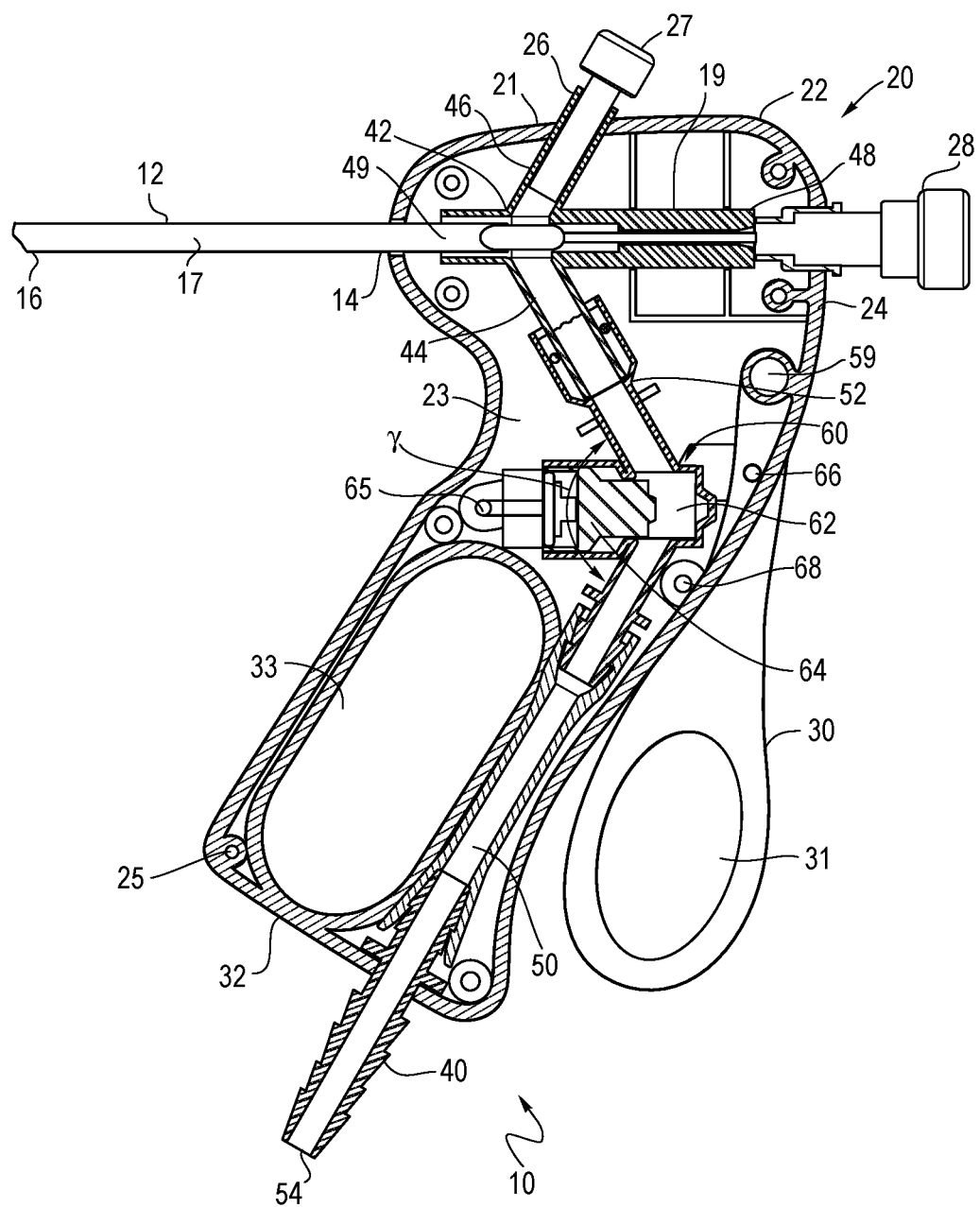
FIG. 2 illustrates an interior view of the medical device of FIG. 1.
Figure 3:
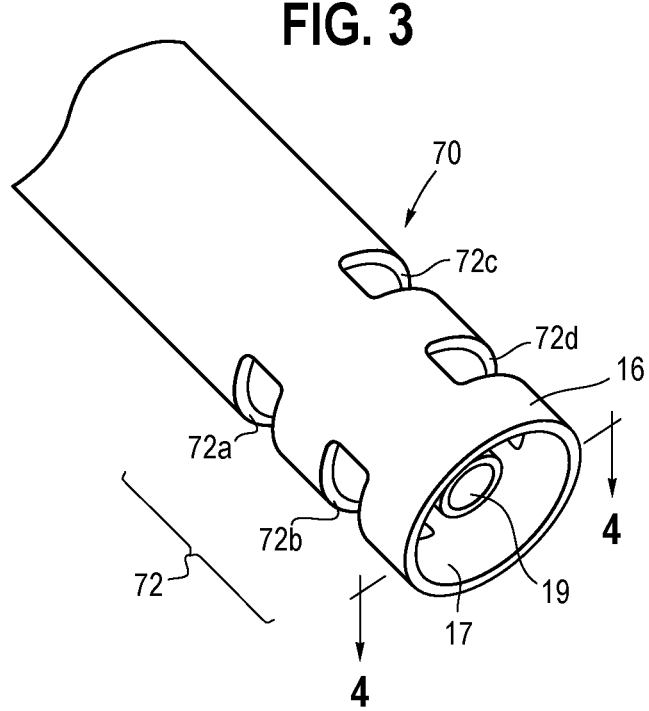
FIG. 3 illustrates an embodiment of a distal end of the catheter of the medical device of FIG. 1.

Referring to the figures, an example medical device 10, is useful in controlling suction during lithography procedures is provided. In example embodiments, the kidney stones are reduced in size, e.g., fragmented, by a procedure in which laser energy, electro-hydraulic energy, or sound energy is applied to reduce the kidney stones in size for easier removal, as described in greater detail below. Referring further generally to FIGS. 1-3, for example, a medical device comprising a catheter 12 having one or more lumens (not shown) and extending between a proximal end 14 and an opposing distal end 16 of the catheter. In example embodiments, the catheter 12 may be a semi-rigid tube that does not deflect appreciably in use. The medical device 10 may be used with a scope, such as an endoscope or a nephroscope, in which the surgeon inserts medical device 10 and catheter 12 into an appropriate channel in the scope. The endoscope allows the surgeon to view the operating field as the surgeon maneuvers the endoscope and the catheter 10 to disrupt and remove foreign bodies within the patient, such as kidney stones. In example embodiments, catheter 12 is sufficiently rigid for the surgeon to deflect and maneuver the scope by using outer catheter 12 of medical device 10. Catheter 12 is made from a biocompatible material, such as polyurethane, polyethylene, tetrafluoroethylene, polytetrafluoroethylene, fluorinated ethylene propylene, nylon, PEBAX®, or the like.

In example embodiments, catheter 12 has a length of 10 inches (25 centimeters (cm)) to 20.00 inches (50 cm), and, more particularly, a length of 13.5 inches (33.75 cm) to 17 inches (42.5 cm), suitable to allow the surgeon to reach the multiple poles of the patient's kidney by percutaneous introduction, for example. In a preferred embodiment, catheter 12 has a length of 15.2 inches (38 cm). In alternative embodiments, catheter may have any suitable length less than 10.0 inches or greater than 20.00 inches. Catheter 12 has an outer diameter of 10 Fr to 15 Fr, and, more particularly, an outer diameter of 11 Fr to 13 Fr. In one example embodiment, catheter 12 has an outer diameter of 11.6 Fr. An inner diameter of catheter 12 may range from 3 Fr. to 8 Fr, and more particularly 4 Fr. to 7 Fr. In a preferred embodiment, catheter 12 has an inner diameter of 6 Fr.

Referring to FIG. 1, an example embodiment is illustrated. A medical device 10 comprising a catheter 12 having a proximal end 14 and a distal end 16 is present. The medical device further includes a handle assembly 20. The handle assembly includes a first section 22 and a second section 24. A portion of the proximal end 12 of the catheter is engaged with the first section 22 of the handle assembly 20. The handle assembly 20 includes an irrigation port 26 and a connector 28 (e.g. Touhy-Borst connector) that may be utilized by a user of the medical device 10. In example embodiments, the irrigation port 26 is in fluid communication with a lumen of the catheter 12. The irrigation port 26 may include a fitting such as a luer lock hub 27 for introducing and aspirating fluids therethrough in conventional fashion. The connector 28 may be used to introduce additional medical devices for use with the procedure, such as a probe or laser fiber. A vacuum port 40 is included on the second section 24 of the handle assembly 20. The vacuum port 40 is in fluid communication with an interior passageway (not shown) of the medical device 10 and a lumen of the catheter 12.

The handle assembly 20 may comprise any suitable biocompatible material, including, but not limited to, material, including by injection molding and may comprise materials such as an elastomeric polymer or other suitable biocompatible polymer. For example, the handle assembly 20 may be formed from polymers such as polyether-amide block co-polymer (PEBAX®), nylon (polyamides), polyolefins, polyesters, polycarbonates polyurethanes, polydimethyl siloxane, acrylonitrile butadiene styrene (ABS), high density polyethylene (HDPE), rubber, polyisoprene (i.e., synthetic rubbers), and polytetrafluoroethylene. Extrusion or another high temperature processing, such as injection molding, compacting, ultrasonic or radio frequency sinerting, and slot coating can form the handle assembly 20. In a particular embodiment, the handle assembly 20 may comprise two halves that are injection molded from ABS. In such an embodiment, the two halves of the handle assembly 20 may configured to mate together at a specific location and the connection may be configured for snap fit or interlocking engagement.

The second section 24 of the handle assembly 20 includes an actuator assembly 30 and a gripping region 32. As will be discussed in further detail below, the actuator 30 is pivotable with respect to the second section 24 of the handle assembly 20. In such a configuration, the actuator 30 may operate in cooperation with the gripping region 32 of the second section 24 in a fashion similar to scissors. The actuator 30 includes an ergonomically-shaped opening 31 and configured to receive a thumb of the hand of the user of the medical device 10. The gripping region 32 of the second section 24 of the handle assembly 20 includes an ergonomically-shaped opening 33 configured to receive the remaining fingers of the hand of the user.

As shown in FIG. 1, the second section 24 of the handle assembly 20 is positioned at an angle with respect to the first section 22 of the handle assembly. Particularly, the second section 24 of the handle assembly 20 may extend in such a way that angle α is formed between the first section 22 of the handle assembly 20 and the second section 24 of the handle assembly 20. In example embodiments, the angle α formed by the second section 24 of the handle assembly 20 with respect to the first section 22 of the handle assembly 20 is an acute angle (i.e. an angle less than 90). In some embodiments, the angle α formed by the second section 24 of the handle assembly 20 with respect to the first section 22 of the handle assembly 20 ranges from between 25° and 85°. More particularly, the angle α formed by the second section 24 of the handle assembly 20 with respect to the first section 22 of the handle assembly 20 ranges from between 40° and 70°. In one particular embodiment, the angle α formed by the second section 24 of the handle assembly 20 with respect to the first section 22 of the handle assembly 20 is about 45°. This angled configuration of the second section 24 of the handle assembly 20 with respect to the first section 22 provides ergonomic advantages, including reduced load and stress upon the wrist of the user of the medical device 10 when the user is holding the medical device 10. Further, the angled configuration of the second section 24 of the handle assembly 20 acknowledges the natural angles between the gripping portion of the hand, the wrist, and the forearm of the user. Accordingly, the medical device 10 allows the user to reduce wrist flexion, extension or ulnar or radial deviation, allowing the user to maintain a more neutral wrist posture. Moreover, the angled configuration of the second section 24 of the handle assembly 20 makes the device more accessible from its position relative to a hub of a scope.

FIG. 2 illustrates an interior view of the medical device 10. As shown, the medical device 10 includes a catheter 12 having a proximal end 14 and a distal end 16 is present. The medical device further includes a handle assembly 20. The handle assembly 20 comprises a body 21 defining an interior surface 23 and includes a first section 22 and a second section 24. The proximal end 14 of the catheter 12 is engaged with and disposed through the first section 22 of the handle assembly. As shown, the proximal end 14 of the catheter 12 includes multiple lumens: a large lumen 17 and a small lumen 19. The large lumen 17 and the small lumen 19 are arranged and aligned concentrically along a longitudinal axis of the catheter 12 to minimize mechanical interference. The small lumen 19 is designed and configured to provide access for the introduction of medical devices having a range of diameters, such as laser fibers for use during lithotripsy. The large lumen 17 is designed and configured to provide sufficient space for the extraction of fluid, soft tissue and stone fragments when used with a vacuum source, as discussed below. The handle assembly 20 includes an irrigation port 26 and a connector 28 (e.g. Touhy-Borst connector) that may be utilized by a user of the medical device 10. The irrigation port 26 may include a fitting such as a luer lock hub 27 for introducing and aspirating fluids therethrough in conventional fashion. The small lumen 19 is sealingly connected to the connector 28, thus allowing a user to introduce additional medical devices for use with the procedure, such as a probe or laser fiber through the connector 28. In this embodiment, the handle assembly 20 may include snap-fit connectors 25 to secure two halves of the handle. A vacuum port 40 is included on the second section 24 of the handle assembly 20. The vacuum port 40 may include a universal adaptor in order to allow for connection to a vacuum source. An interior passageway 50, or lumen, is disposed within the interior surface 23 of the handle assembly 20. The interior passageway 50 is in fluid communication with the vacuum port 40 and the large lumen 17 of the catheter. The interior passageway includes a first end 52 and a second end 54. As shown, the second end 54 is adjacent to the vacuum port 40 and the first end is adjacent to the large lumen 17. In example embodiments, the interior passageway 50 may be transverse to the catheter 12. In alternative embodiments, the interior passage may have an angled configuration with respect to the catheter 12. As shown, the interior passageway 50 forms an obtuse angle γ with respect to the catheter 12. This particular angled configuration running through the interior cavity of the handle assembly 20 provides a less tortuous path for stone fragments during removal. Accordingly these stone fragments are more easily expelled from the body of a patient when the medical device 10 is used for a lithotripsy procedure.

The medical device 10 further includes a hub 42 having a first port 44, a second port 46, a third port 48, and a central passageway 49. As shown, the hub 42 provides an engagement point for the cannula 12, the irrigation port 26, the connector 28, and the vacuum port 40. Particularly, the proximal end 14 of the cannula 12 is engaged the central passageway 49 of the hub 42, placing the large lumen 19 of the cannula 12 in fluid communication with the central passageway 49 of the hub 42. The first port 44 is engaged with the first end 52 of the interior passageway 50. This configuration places the interior passageway 50 in fluid communication with the large lumen 17 of the catheter 12 via the central passageway 49 of the hub 42. Accordingly, during use, debris accumulated from the lithotripsy procedure may be removed from the body via vacuum through the interior passageway 50. The second port 46 is engaged with irrigation port 26. This configuration places the irrigation port 26 in fluid communication with the large lumen 17 of the catheter 12 via the central passageway 49 of the hub 42. Accordingly, a user has the ability to irrigate the large lumen 17 of the catheter 12 to flush out any clots or clogs during the lithotripsy procedure. The third port 48 is engaged with the connector 28.

The second section 24 of the handle assembly 20 includes an actuator assembly 30 and a gripping region 32. The actuator 30 is pivotable with respect to the second section 24 of the handle assembly 20. The actuator 30 may be pivotably connected to the second section 24 by a pivot pin 59. In such a configuration, the actuator 30 may operate in cooperation with the gripping region 32 of the second section in a fashion similar to scissors. The actuator 30 includes an ergonomically-shaped opening 31 and configured to receive a thumb of the hand of the user of the medical device 10. The gripping region 32 of the second section 24 of the handle assembly 20 includes an ergonomically-shaped opening 33 configured to receive the remaining fingers of the hand of the user. The actuator 30 is designed to work in conjunction with a valve assembly 60. The valve assembly 60 is positioned within the interior passageway 50 and comprises a valve housing 62 and a valve piston 64. The valve piston 64 may be secured to the valve housing 62 through the use of a suitable device, such as a gudgeon pin 65. In alternative embodiments, the valve assembly 60 may have other suitable configurations.

Trigger links 66 and 68 may be engaged with the valve assembly 60 and the actuator 30. Thus, movement of the actuator 30 will control the movement of the valve piston 64 within the valve housing 62 in order to open or close the valve assembly 60. In this embodiment, the valve assembly 60 is biased to the closed position by vacuum itself. Thus, the valve assembly 60 is held in the closed position while the actuator 30 is placed in a rest position. Movement of the actuator 30 in the direction of the gripping region 32 of the second section 24 of the handle assembly 20 translates movement of the valve piston 64 from the closed position to an open position. The actuator 30 may allow for incremental movement of the valve piston 64 within the valve housing 62. Thus, the actuator 30 provides a user of the medical device 10 the ability to control the movement of the valve piston 64 within the valve housing 62 in order to modulate the flow of the vacuum during use of the device.

Figure 4:
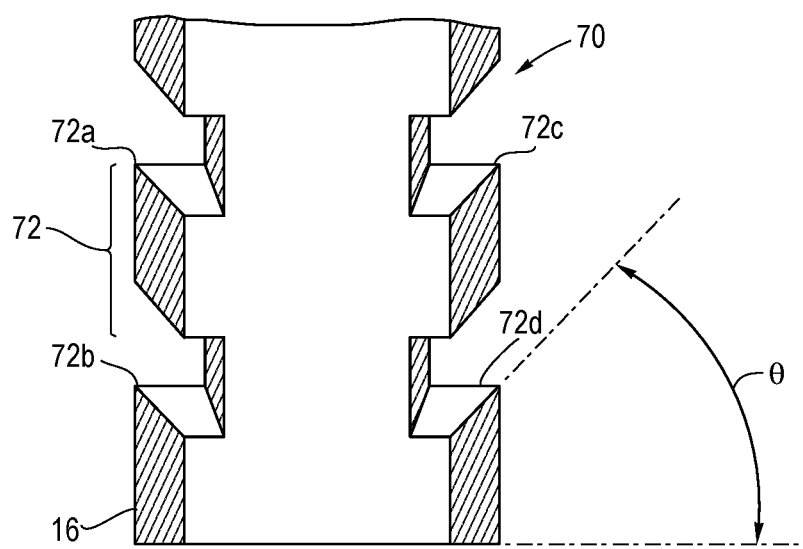
FIG. 4 illustrates a cross-sectional view of the distal end of the catheter of FIG. 3.

FIGS. 3 and 4 illustrates a distal end 16 of the catheter 12 of the medical device. The catheter 12 includes a large lumen 17 and a small lumen 19. As shown, the large lumen 17 and the small lumen 19 are arranged and aligned concentrically along a longitudinal axis of the catheter 12 to minimize mechanical interference. As shown, the catheter 12 includes a vented region 70. The vented region 70 may include one or more discrete vents 72. In the present embodiment, the vented region includes four vents 72a, 72b, 72c, and 72d. The vents 72 may be configured such that a pair of vents is formed on opposing sides of the catheter 12. For example, vents 72a and 72b form a pair of vents 72 and vents 72c and 72d form a second pair of vents. In example embodiments, the number of vents may range from 1 vent to 10 vents, more particularly 2 vents to 6 vents. The vents 72 of the vented region 70 may formed into the outer edges of the distal end 16 of the catheter 12 by any suitable means, including, but not limited to, laser cutting, water-jet cutting and photochemical etching. In a particular embodiment, the edges 74 of the vents 72 of the vented region 70 may formed by laser cutting. An advantage of this particular embodiment is that laser cutting may make the vents 72 smooth and snag-free. In addition, the vents 72a, 72b, 72c, and 72d of the vented region 70 may help prevent tissue from being pulled into the distal end 16 of the catheter 12 when vacuum is applied by creating alternative pathways for suction to take place, thereby minimizing damage tissue.

As shown in more detail in FIG. 4, the vents 72a, 72b, 72c, and 72d may have an angled configuration θ with respect to the distal end 16 of the catheter 12. In example embodiments, the angle θ with respect to the distal end 16 of the catheter 12 is an acute angle (i.e. an angle less than 90). In alternative embodiments, the angle θ with respect to the distal end 16 of the catheter 12 is an obtuse angle (i.e. an angle greater than 90). In a particular embodiments, the angle θ with respect to the distal end 16 of the catheter 12 is an acute angle ranging from 25° to 85°, more particularly, 35° to 65°. The cross-sectional area of the 72a, 72b, 72c, and 72d as compared to the distal end 16 of the catheter 12 may also reduce risk by balancing performance of suction and minimizing tissue damage. The angled configuration of the vents also serve to moderate velocity of the fluid flow, while simultaneously directing most of the suction provided by the vacuum to remove fragments, soft tissue, and fluid from the body of a patient. In addition, the angled configuration θ of the vents 72a, 72b, 72c, and 72d allows for vacuuming proximal to the distal end 16 of the catheter 12. This improvement reduces the amount of procedural time by minimizing the amount of movement of the catheter 12 necessary to properly remove the fragments, soft tissue, and/or fluid. The angled configuration θ of the angled configuration θ of the vents 72a, 72b, 72c, and 72d also reduce the amount of debris (i.e. material and/or dust) that may be move distally during the procedure, which may increase visibility at the distal end 16 of the catheter 12.

In the use of medical device 10 in a percutaneous kidney stone removal procedure, the standard preparatory procedures and standard auxiliary equipment are used. Initially, a suitable percutaneous tract to the kidney in the patient's body is provided and an adequate visualization of the collecting system of the kidney by means of a scope is established through the percutaneous track. Prior to placement within the percutaneous tract, the user may attached the medical device 10 to a vacuum source via the vacuum port 40. The user may adjust the amount of vacuum depending on the needs of the user and the condition of the patient. Once connected to the vacuum source, cannula 12 is advanced through the percutaneous track to the target site. This advancement is accomplished by manually feeding medical device 10 through a working channel in the scope. When distal end 16 of the cannula 20 reaches the target area as determined by visual inspection of the scope, the operator may further advance a laser assembly through the small lumen 19 of the catheter 12.

Once the laser assembly extends beyond the distal end 16 of the catheter 12 to the desired distance, the laser assembly is secured to the medical device 10 with the connector 28. The operator may utilize the laser assembly to fragment the stone to facilitate removal of smaller pieces of stone from within the patient's kidney. During this process, the operator may grasp the medical device 10 and control the flow of the vacuum through use of the actuator 30. The use of the laser assembly in cooperation with the medical device 10 allows for localizing the area in which the kidney stone resides, as well as producing smaller stone fragments that are easier to remove. This process also minimizes surgical time and reduces the need for clear visualization during the procedure. Furthermore, the actuator 30 provides the operator additional and more intuitive control of the flow of the vacuum. As discussed with reference to FIG. 2, the user may move the actuator 30 in the direction of the gripping region 32 of the second section 24 of the handle assembly 20, which in turn translates movement of the valve piston 64 from the closed position to an open position. The actuator 30 provides a user of the medical device 10 the ability to control the movement of the valve piston 64 within the valve housing 62 in order to modulate the flow of the vacuum during use of the device. The process of fragmenting the stone and removing the stone fragments from the body may be repeated as necessary.

Should the medical device 10 become clogged with stone fragments, soft tissue and the like, the medical device 10 may be removed from the patient, the actuator 30 may be moved in a direction away from the gripping portion 32 of the handle assembly 20, which translates into movement of the valve piston 64 into a closed position. Once the medical device 10 is removed from the patient, the obstructed lumen may be flushed or irrigated via the irrigation port 26. In practice, the user may attached a syringe to the luer lock hub 27 of the irrigation port 26 and introduce a fluid, such as saline, into the obstructed lumen do clear the device.

Figure 5:
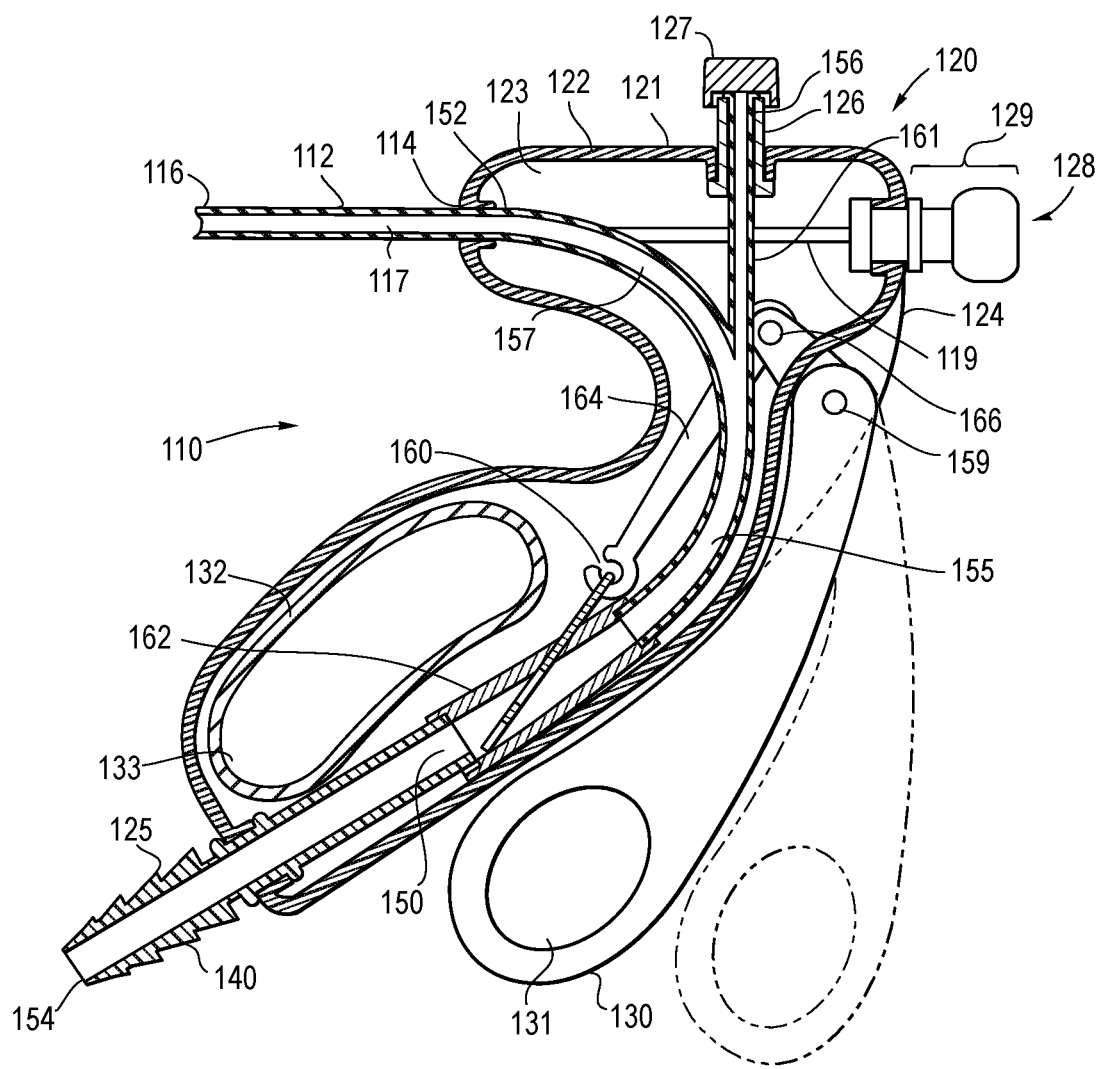
FIG. 5 illustrates an interior view of an alternative embodiment of a medical device for stone management.

FIG. 5 illustrates an interior view of an alternative embodiment medical device 110. As shown, the medical device 110 includes a catheter 112 having a proximal end 114 and a distal end 116 is present. The medical device 110 further includes a handle assembly 120. The handle assembly 120 comprises a body 121 defining an interior surface 123 and includes a first section 122 and a second section 124. The proximal end 114 of the catheter 12 is engaged with and disposed through the first section 122 of the handle assembly. As shown, the proximal end 114 of the catheter 112 includes multiple lumens: a large lumen 117 and a small lumen 119. The large lumen 117 and the small lumen 119 are arranged and aligned such that they are concentrically along a longitudinal axis of the catheter 112 as they exit the first section 122 of the handle assembly 120. The small lumen 119 is designed and configured to provide access for the introduction of medical devices having a range of diameters, such as laser fibers for use during lithotripsy. The large lumen 117 is designed and configured to provide sufficient space for the extraction of fluid, soft tissue and stone fragments when used with a vacuum source.

The handle assembly 120 includes an irrigation port 126 and a connector 128 (e.g. Touhy-Borst connector 129) that may be utilized by a user of the medical device 110. The irrigation port 126 includes a fitting such as a luer lock hub 127 for introducing and aspirating fluids therethrough in conventional fashion. The small lumen 119 is sealingly connected to the connector 128, thus allowing a user to introduce additional medical devices for use with the procedure, such as a probe or laser fiber through the connector 128. A vacuum port 140 is included on the second section 124 of the handle assembly 120. The vacuum port 140 may include a universal adaptor 125 in order to allow for connection to a vacuum source. An interior passageway 150, or lumen, is disposed within the interior surface 123 of the handle assembly 120. The interior passageway 150 is in fluid communication with the vacuum port 140 and the large lumen 117 of the catheter. As shown, the interior passageway 150 is bifurcated creating a main lumen 155, a first branch 157 and a second branch 161. The interior passageway 150 includes a first end 152, a second end 154, and a third end 156. As shown, the second end 154, which is a part of the main lumen 155, is adjacent to the vacuum port 140 and the first end 152, which is a part of the first branch 157, is adjacent to the large lumen 117. Thus, the larger lumen 117 of the catheter is in fluid communication with the vacuum port 140. The third end 156, which is a part of the second branch 159, is adjacent to the irrigation port 126 of the handle assembly 120. Thus, the irrigation port is in fluid communication with the vacuum port 140 of the handle assembly 120.

In example embodiments, the first branch 157 of the interior passageway 150 may be transverse to the main lumen 155. In alternative embodiments, the first branch 157 of the interior passage 150 may have a curved configuration with respect to the main lumen 155. As shown, the first branch 157 of the interior passageway 150 has a curved configuration. This particular curved configuration of the first branch 157 provides a less tortuous path for stone fragments during removal. Accordingly these stone fragments are more easily expelled from the body of a patient when the medical device 110 is used for a lithotripsy procedure.

The second section 124 of the handle assembly 120 includes an actuator assembly 130 and a gripping region 132. The actuator 130 is pivotable with respect to the second section 124 of the handle assembly 120. The actuator 130 may be pivotably connected to the second section 124 by a pivot pin 159. In such a configuration, the actuator 130 may operate in cooperation with the gripping region 132 of the second section in a fashion similar to scissors. The actuator 130 includes an ergonomically-shaped opening 131 and configured to receive a thumb of the hand of the user of the medical device 110. The gripping region 132 of the second section 124 of the handle assembly 120 includes an ergonomically-shaped opening 133 configured to receive the remaining fingers of the hand of the user. The actuator 130 is designed to work in conjunction with a valve assembly 160. The valve assembly 160 is positioned within the main lumen 155 of the interior passageway 150 and comprises a sliding reed valve 162. A link 164 is provided to connect the sliding reed valve 162 to load point 166 on the actuator 130. Thus, movement of the actuator 130 will control the movement of the reed valve 162 in order to open or close the valve assembly 160. In this embodiment, the valve assembly 160 is biased to the closed position by vacuum itself. Thus, the valve assembly 160 is held in the closed position while the actuator 130 is placed in a rest position. Movement of the actuator 130 in the direction of the gripping region 132 of the second section 124 of the handle assembly 120 translates movement of the reed valve 162 from the closed position to an open position. The actuator 130 may allow for incremental movement of the reed valve 162. Thus, the actuator 130 provides a user of the medical device 110 the ability to control the movement of the reed valve 162 in order to modulate the flow of the vacuum during use of the device.

Figure 6:
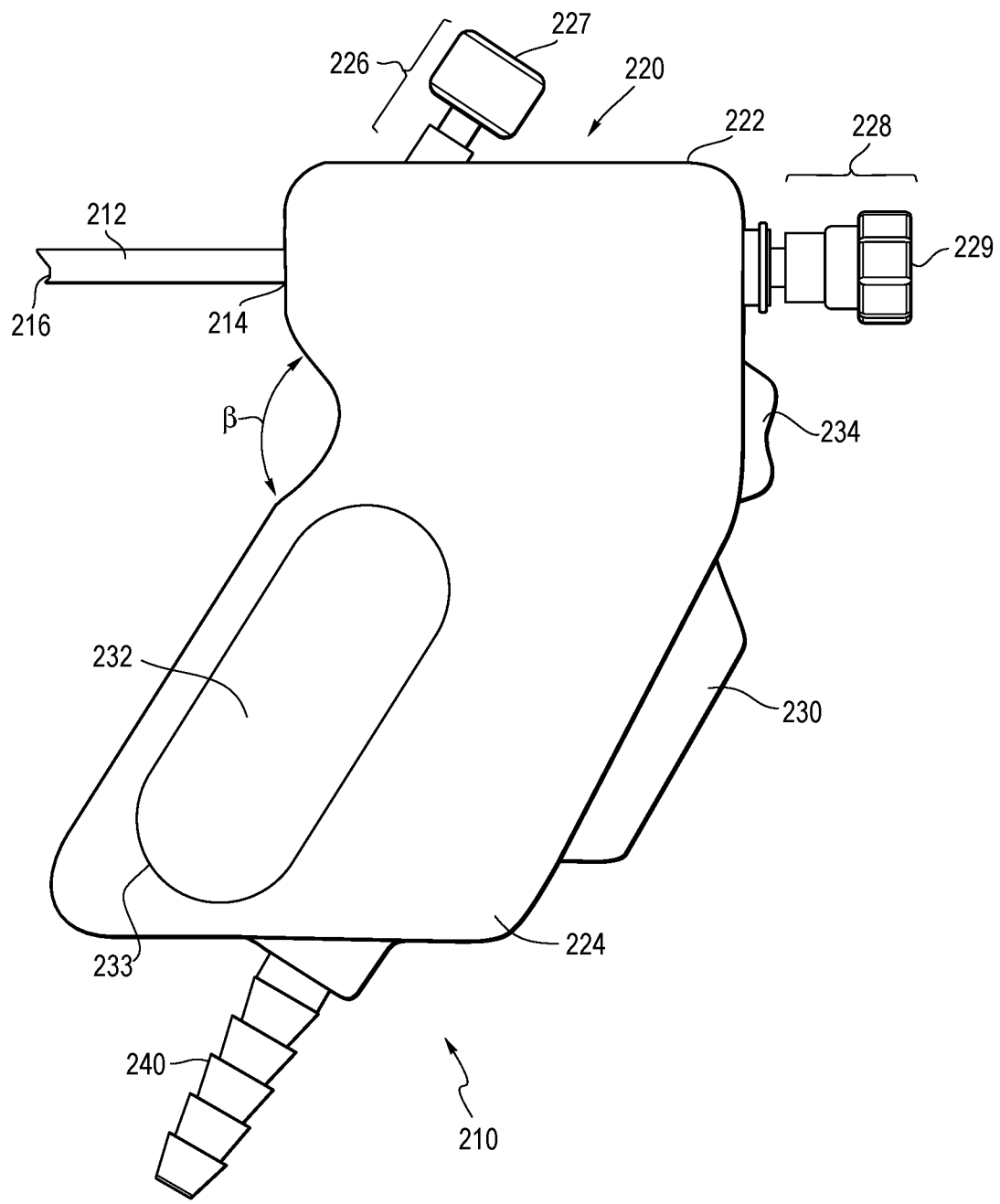
FIG. 6 illustrates an exterior view of an alternative embodiment of a medical device for stone management.

FIG. 6 illustrates an exterior view of an alternative embodiment of a medical device 210. The medical device 210 comprising a catheter 212 having a proximal end 214 and a distal end 216 is present. The medical device further includes a handle assembly 220. The handle assembly includes a first section 222 and a second section 224. A portion of the proximal end 212 of the catheter is engaged with the first section 222 of the handle assembly 220. The handle assembly 220 includes an irrigation port 226 and a connector 228 (e.g. Touhy-Borst connector) that may be utilized by a user of the medical device 210. In example embodiments, the irrigation port 226 is in fluid communication with a lumen of the catheter 212. The irrigation port 226 may include a fitting such as a luer lock hub 227 for introducing and aspirating fluids therethrough in conventional fashion. The connector 228 may be used to introduce additional medical devices for use with the procedure, such as a probe or laser fiber. A vacuum port 240 is included on the second section 224 of the handle assembly 220. The vacuum port 240 is in fluid communication with an interior passageway (not shown) of the medical device 210 and a lumen of the catheter 212.

The second section 224 of the handle assembly 220 includes an actuator assembly 230, a gripping region 232, and sliding lock 234. As will be discussed in further detail below, the actuator 230 may be squeezable or compressible with respect to the second section 224 of the handle assembly 220. The gripping region 232 of the second section 224 of the handle assembly 220 includes an ergonomically-shaped opening 233 configured to receive the remaining fingers of the hand of the user.

As shown in FIG. 6, the second section 224 of the handle assembly 220 is positioned at an angle with respect to the first section 222 of the handle assembly 220. Particularly, the second section 224 of the handle assembly 220 may extend in such a way that angle β is formed between the first section 222 of the handle assembly 220 and the second section 224 of the handle assembly 220. In example embodiments, the angle β formed by the second section 224 of the handle assembly 220 with respect to the first section 222 of the handle assembly 220 is an acute angle (i.e. an angle less than 90). In some embodiments, the angle β formed by the second section 224 of the handle assembly 220 with respect to the first section 222 of the handle assembly 220 ranges from between 25° and 85°. More particularly, the angle β formed by the second section 224 of the handle assembly 220 with respect to the first section 222 of the handle assembly 220 ranges from between 40° and 70°. In one particular embodiment, the angle β formed by the second section 224 of the handle assembly 220 with respect to the first section 222 of the handle assembly 220 is about 45°. This angled configuration of the second section 224 of the handle assembly 220 with respect to the first section 222 provides ergonomic advantages, including reduced load and stress upon the wrist of the user of the medical device 210 when the user is holding the medical device 210. Further, the angled configuration of the second section 224 of the handle assembly 220 acknowledges the natural angles between the gripping portion of the hand, the wrist, and the forearm of the user. Accordingly, the medical device 210 allows the user to reduce wrist flexion, extension or ulnar or radial deviation, allowing the user to maintain a more neutral wrist posture. Moreover, the angled configuration of the second section 24 of the handle assembly 220 makes the device more accessible from its position relative to a hub of a scope.

Figure 7:
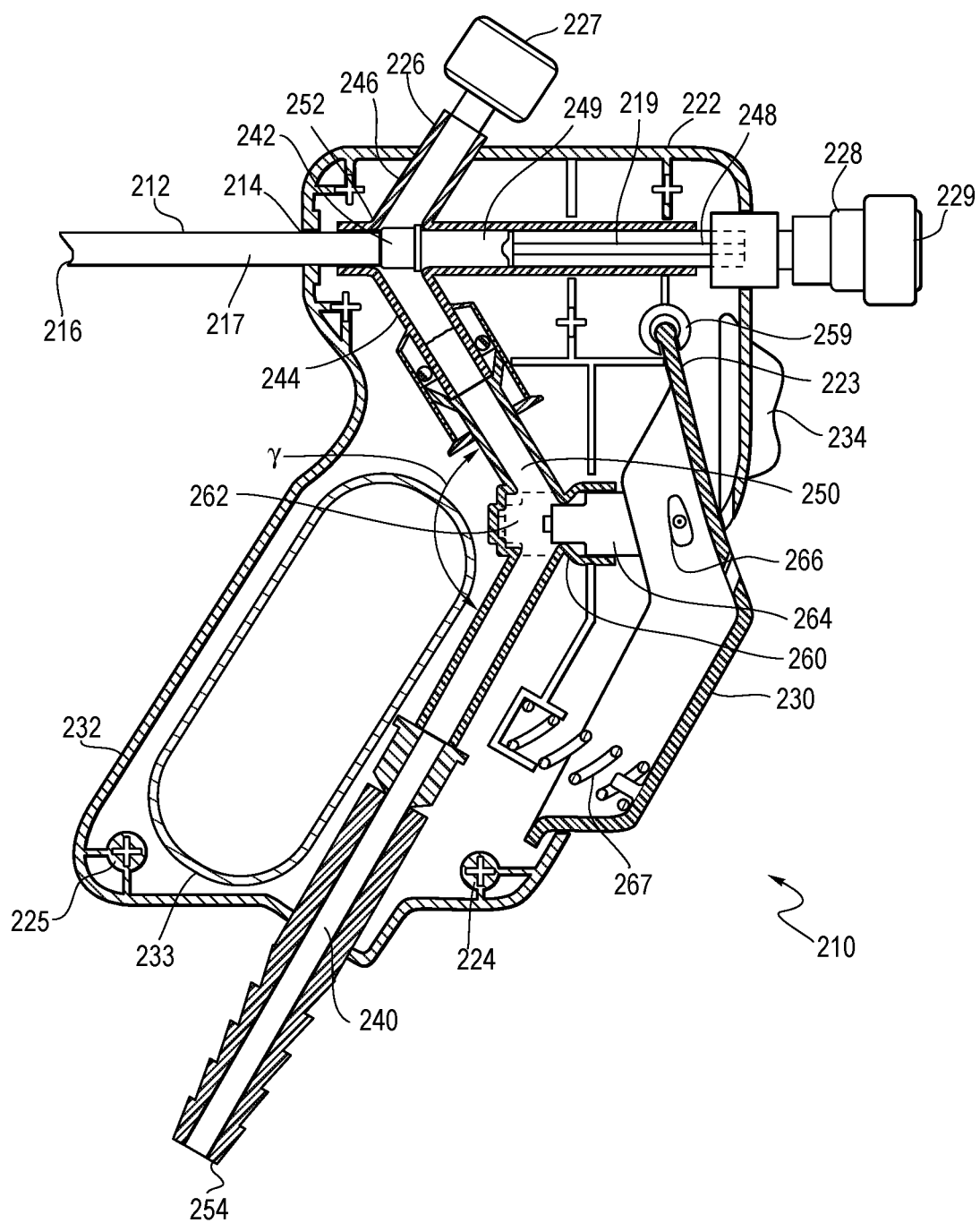
FIG. 7 illustrates an interior view of the embodiment of FIG. 5.

FIG. 7 illustrates an interior view of the medical device 210. As shown, the medical device 210 includes a catheter 212 having a proximal end 214 and a distal end 216 is present. The medical device further includes a handle assembly 220. The handle assembly 220 comprises a body 221 defining an interior surface 223 and includes a first section 222 and a second section 224. The proximal end 214 of the catheter 212 is engaged with and disposed through the first section 222 of the handle assembly. As shown, the proximal end 214 of the catheter 212 includes multiple lumens: a large lumen 217 and a small lumen 219. The large lumen 217 and the small lumen 219 are arranged and aligned concentrically along a longitudinal axis of the catheter 212 to minimize mechanical interference. The small lumen 219 is designed and configured to provide access for the introduction of medical devices having a range of diameters, such as laser fibers for use during lithotripsy. The large lumen 217 is designed and configured to provide sufficient space for the extraction of fluid, soft tissue and stone fragments when used with a vacuum source, as discussed below. The handle assembly 220 includes an irrigation port 226 and a connector 228 (e.g. Touhy-Borst connector 229) that may be utilized by a user of the medical device 210. The irrigation port 226 may include a fitting such as a luer lock hub 227 for introducing and aspirating fluids therethrough in conventional fashion. The small lumen 219 is sealingly connected to the connector 228, thus allowing a user to introduce additional medical devices for use with the procedure, such as a probe or laser fiber through the connector 228. In this embodiment, the handle assembly 220 may include snap-fit connectors 225 to secure two halves of the handle. A vacuum port 240 is included on the second section 224 of the handle assembly 220. The vacuum port 240 may include a universal adaptor in order to allow for connection to a vacuum source. An interior passageway 250, or lumen, is disposed within the interior surface 223 of the handle assembly 220. The interior passageway 250 is in fluid communication with the vacuum port 240 and the large lumen 217 of the catheter. The interior passageway includes a first end 252 and a second end 254. As shown, the second end 254 is adjacent to the vacuum port 240 and the first end 252 is adjacent to the large lumen 217. In example embodiments, the interior passageway 250 may be transverse to the catheter 212. In alternative embodiments, the interior passage may have an angled configuration with respect to the catheter 212. As shown, the interior passageway 250 forms an obtuse angle γ with respect to the catheter 212. This particular angled configuration running through the interior cavity of the handle assembly 220 provides a less tortuous path for stone fragments during removal. Accordingly these stone fragments are more easily expelled from the body of a patient when the medical device 210 is used for a lithotripsy procedure.

The medical device 210 further includes a hub 242 having a first port 244, a second port 246, a third port 248, and a central passageway 249. As shown, the hub 242 provides an engagement point for the cannula 212, the irrigation port 226, the connector 228, and the vacuum port 240. Particularly, the proximal end 214 of the cannula 212 is engaged the central passageway 249 of the hub 242, placing the large lumen 217 of the cannula 212 in fluid communication with the central passageway 249 of the hub 242. The first port 246 is engaged with the first end 252 of the interior passageway 250. This configuration places the interior passageway 250 in fluid communication with the large lumen 217 of the catheter 212 via the central passageway 249 of the hub 242. Accordingly, during use, debris accumulated from the lithotripsy procedure may be removed from the body via vacuum through the interior passageway 250. The second port 246 is engaged with irrigation port 226. This configuration places the irrigation port 226 in fluid communication with the large lumen 217 of the catheter 212 via the central passageway 249 of the hub 242. Accordingly, a user has the ability to irrigate the large lumen 217 of the catheter 212 to flush out any clots or clogs during the lithotripsy procedure. The third port 248 is engaged with the connector 228.

The second section 224 of the handle assembly 220 includes an actuator assembly 230, a gripping region 232, and a sliding lock 234. The actuator 230 is squeezable trigger and may be moved with respect to the second section 224 of the handle assembly 220. The actuator 230 may be connected to the second section 224 of the handle 220 by a pivot pin 259. The actuator 230 is designed to work in conjunction with a valve assembly 260. The valve assembly 260 is positioned within the interior passageway 250 and comprises a valve housing 262 and a valve piston 264. The valve piston 264 may be secured to the valve housing 262 through the use of a suitable device, such as a gudgeon pin. In alternative embodiments, the valve assembly 260 may have other suitable configurations.

A trigger link 266 may be engaged with the valve assembly 260 and the actuator 230. Thus, movement of the actuator 230 will control the movement of the valve piston 264 within the valve housing 262 in order to open or close the valve assembly 260. In this embodiment, the valve assembly 260 is biased to the open position by a spring 267, such as a compression spring. Thus, the valve assembly 260 is held in the open position while the actuator 230 is placed in a rest position. Movement of the actuator 230 in the direction of the gripping region 232 of the second section 224 of the handle assembly 220 causes the compression spring to compress, which translates to movement of the valve piston 264 from the open position to a closed position. The actuator 230 may allow for incremental movement of the valve piston 264 within the valve housing 262. Thus, the actuator 230 provides a user of the medical device 210 the ability to control the movement of the valve piston 264 within the valve housing 262 in order to modulate the flow of the vacuum during use of the device. The actuator 230 may be secured in the closed position by the sliding lock 234. In other embodiments, the valve assembly 260 may be biased by alternative devices including, but not limited to, a miniature hydraulic cylinder or gas cylinder; torsion springs; leaf springs; memory foam; and flat coil springs.

In the use of medical device 210 in a percutaneous kidney stone removal procedure, the standard preparatory procedures and standard auxiliary equipment are used. Initially, a suitable percutaneous tract to the kidney in the patient's body is provided and an adequate visualization of the collecting system of the kidney by means of a scope is established through the percutaneous track. Prior to placement within the percutaneous tract, the user may attach the medical device 210 to a vacuum source via the vacuum port 240. The user may adjust the amount of vacuum depending on the needs of the user and the condition of the patient. Once connected to the vacuum source, cannula 212 is advanced through the percutaneous track to the target site. This advancement is accomplished by manually feeding medical device 210 through a working channel in the scope. When distal end 216 of the cannula 220 reaches the target area as determined by visual inspection of the scope, the operator may further advance a laser assembly through the small lumen 219 of the catheter 212.

Once the laser assembly extends beyond the distal end 216 of the catheter 212 to the desired distance, the laser assembly is secured to the medical device 210 with the connector 228. The operator may utilize the laser assembly to fragment the stone to facilitate removal of smaller pieces of stone from within the patient's kidney. During this process, the operator may grasp the medical device 210 and control the flow of the vacuum through use of the actuator 230. The use of the laser assembly in cooperation with the medical device 210 allows for localizing the area in which the kidney stone resides, as well as producing smaller stone fragments that are easier to remove. This process also minimizes surgical time and reduces the need for clear visualization during the procedure. Furthermore, the actuator 230 provides the operator additional and more intuitive control of the flow of the vacuum. As discussed with reference to FIG. 7, the user may move the actuator 230 in the direction of the gripping region 232 of the second section 224 of the handle assembly 220, which in turn translates movement of the valve piston 264 from the open position to an closed position. The actuator 230 provides a user of the medical device 210 the ability to control the movement of the valve piston 264 within the valve housing 262 in order to modulate the flow of the vacuum during use of the device. The process of fragmenting the stone and removing the stone fragments from the body may be repeated as necessary.

Should the medical device 210 become clogged with stone fragments, soft tissue and the like, the medical device 210 may be removed from the patient, the actuator 230 may be moved in a direction toward from the gripping portion 232 of the handle assembly 220, which translates into movement of the valve piston 264 into a closed position. The actuator 230 is locked into this position by the sliding lock 234. Once the medical device 210 is removed from the patient, the obstructed lumen may be flushed or irrigated via the irrigation port 226. In practice, the user may attach a syringe to the luer lock hub 227 of the irrigation port 226 and introduce a fluid, such as saline, into the obstructed lumen do clear the device.

Figure 8A:
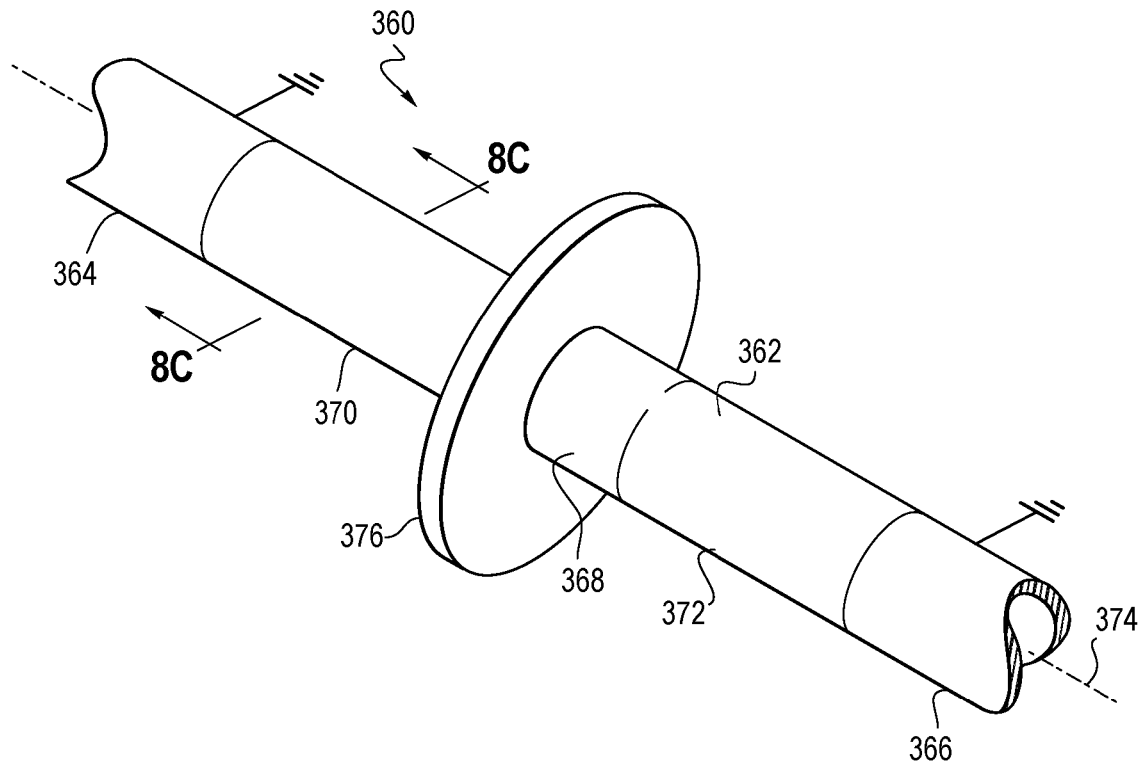
FIGS. 8A-8F illustrate an alternative embodiment of valve for use with an embodiment of a medical device for stone management.

FIGS. 8A-8F illustrate an alternative valve assembly 360 for use with a medical device for stone management according to the present invention. As shown in FIG. 8A, the valve assembly 360 includes a flexible tube 362 comprising a first end 364, a second end 366, an intermediate section 368 positioned between the first end 364 and the second end 366, a first compliant section 370, and a second compliant section 372. The first compliant section 370 is positioned between the intermediate section 368 and the first end 364 of the flexible tube 362. The second compliant section 372 is positioned between the intermediate section 368 and the second end 366 of the flexible tube 362. The first end 364 and the second end 366 of the flexible tube 362 are configured to remain stationary when positioned within an interior body of the medical device and share a common centerline 374. A rotating member 376 is positioned in the intermediate section 368 of the flexible tube 362 and shares a common centerline 374 with the first end 364 and the second end 366. The rotating member 376 is rotatable about an axis that is concentric with the centerline 374. The rotating member 376 is attached to the flexible tube 362 such that torsional loads are transmitted from the former to the latter. The first end 364 of the flexible tube 362 may be positioned proximally and is connected in fluid communication with a vacuum port. The second end 366 of the flexible tube 362 may be positioned such that it is in fluid communication with the distal end of the medical device.

Figure 8B:
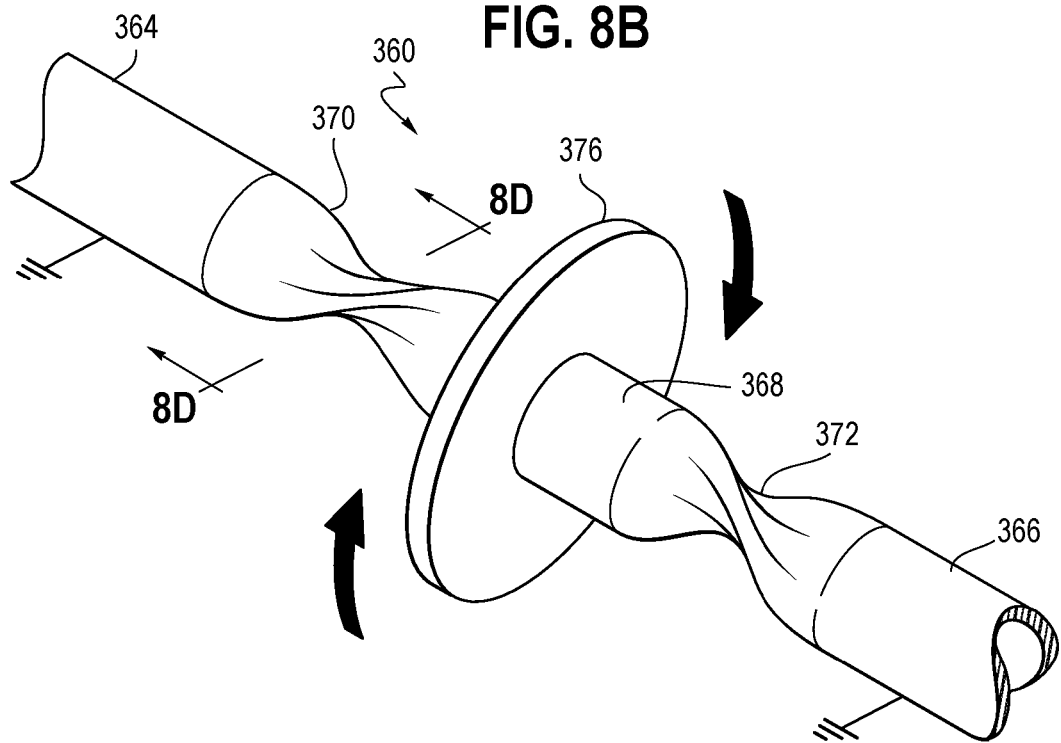
Figure 8C:
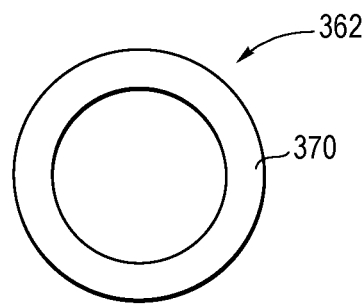
Figure 8D:
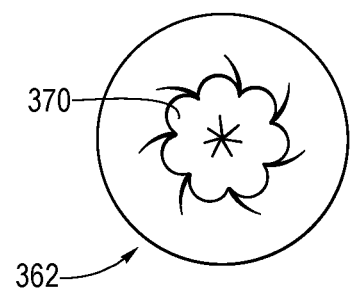

As illustrated by FIG. 8B, rotation of the rotating member 376 causes the first compliant section 370 and the second compliant section 372 to twist in opposite directions, resulting in a reduction in the diameter of the lumen. In example embodiments, the luminal diameter may be variable from 100% patency to less than 1% patency, as shown in FIGS. 8C and 8D. This embodiment includes no components within the lumen of the flexible tube 362, which eliminates possible obstacles that may interfere with the flow or the passage of fragments from the reduction of stone within the patient and may reduce leaks or failure of the valve assembly 360. Further, this embodiment provides a passageway that maintains a round cross-section and provides a straight, low resistance path.

Figure 8E:
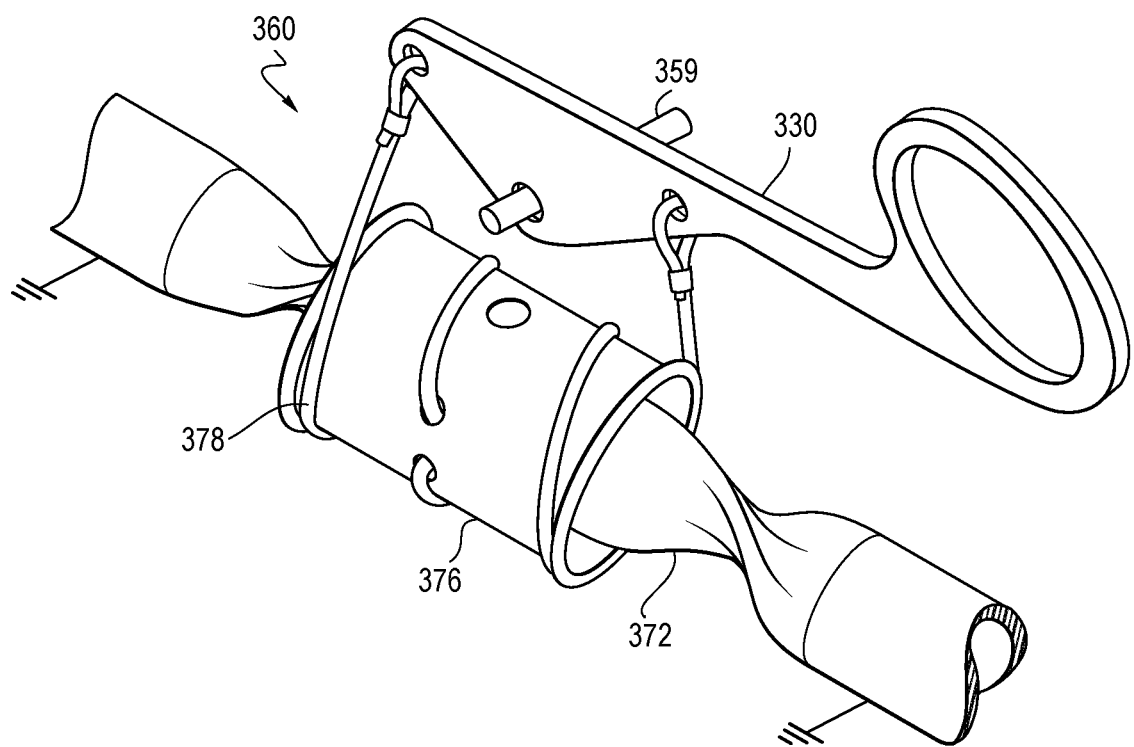

FIG. 8E illustrates the interaction between an actuator 330 and the valve assembly 360. In example embodiments, the actuator 330 is pivotably connected to a medical device (not shown) by a pivot pin or axle 359. The rotating member 376 is acted upon by a kinetic link 378, such as a cable. As shown, the kinetic link 378 connects the actuator 330 to the valve arrangement 360. Movement of the actuator 330 about the axle 359 translates into rotational motion of the rotating member 376 from a first, open position to a second closed position. In alternative embodiments, a biasing spring could be incorporated into the actuator 330 in order to assist with moving the actuator 330 to a given position. A lock or detents may also be used to hold the valve assembly in any given position.

Figure 8F:
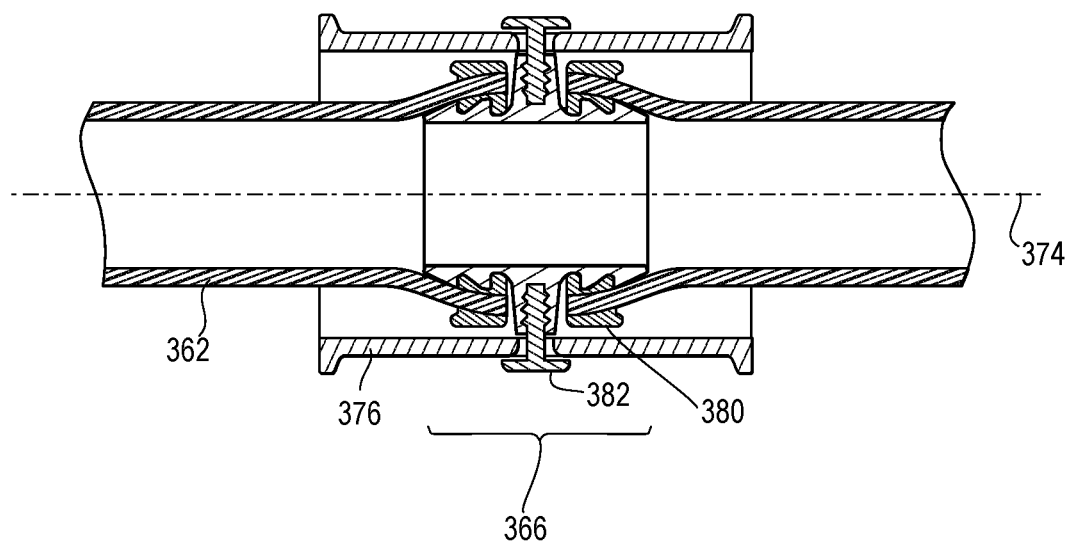

FIG. 8F illustrates a cross-sectional view of the connection between the rotating member 376 and the intermediate section 366 of the flexible tube 362. As shown, the rotating member 376 may be connected to the flexible tube 362 through the use of a heat shrink polymer tube 380. Additional attachment mechanisms 382, such as screws, may be further used to facilitate the connection between the rotating member 376 and the intermediate section 366.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more examples of implementations.

It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Reference throughout this specification to "one embodiment" or "an embodiment" can mean that a particular feature, structure, or characteristic described in connection with a particular embodiment can be included in at least one embodiment of claimed subject matter. Thus, appearances of the phrase "in one embodiment" or "an embodiment" in various places throughout this specification are not necessarily intended to refer to the same embodiment or to any one particular embodiment described. Furthermore, it is to be understood that particular features, structures, or characteristics described can be combined in various ways in one or more embodiments. In general, of course, these and other issues can vary with the particular context of usage. Therefore, the particular context of the description or the usage of these terms can provide helpful guidance regarding inferences to be drawn for that context.

The invention claimed is:

1. A medical device for stone management, comprising:
 a catheter comprising a proximal end, a distal end, and a first lumen and a second lumen disposed therethrough;
 a handle assembly interconnected with the proximal end of the catheter, the handle assembly comprising a body defining an interior cavity, a first section and a second section;
 an interior passageway disposed within the interior cavity and in fluid communication with the first lumen of the catheter; the interior passageway having an angled configuration with respect to the catheter and having a first end and a second end;
 a valve assembly positioned within the interior passageway, the valve assembly moveable between a first position and a second position;
 an actuator assembly engaged with the valve assembly; and
 a vacuum port in fluid communication with the interior passageway and positioned on the second section of the handle;
 wherein the second section of the handle assembly forms an angle with respect to the first section of the handle assembly,
 wherein the actuator allows for incremental movement of the valve assembly between the first position to the second position, and
 wherein the second end of the interior passageway is adjacent to the vacuum port.

2. The medical device of claim 1, further comprising a hub positioned within the interior cavity of the handle assembly, the hub comprising a first port, a second port, third port, and a central passage.

3. The medical device of claim 2, wherein the proximal end of the catheter is in contact with the central passage.

4. The medical device of claim 2, wherein the first end of the interior passageway is in communication with the first port of the hub.

5. The medical device of claim 2, wherein the handle assembly further comprises a connector in communication with the second port of the hub.

6. The medical device of claim 2, wherein the handle assembly further comprises an irrigation port in communication with the second port of the hub.

7. The medical device of claim 1, wherein the actuator includes a moveable arm pivotably connected to the second section of the handle assembly.

8. The medical device of claim 1, wherein the actuator comprises a squeeze trigger.

9. The medical device of claim 1, wherein the distal end of the catheter includes one or more vents.

10. The medical device of claim 9, wherein the one or more vents are angled relative to catheter.

11. The medical device of claim 1, wherein the second section of the handle assembly forms an angle of less than 90 degrees with respect to the first section of the handle assembly.

12. The medical device of claim 11, wherein the second section of the handle assembly forms an angle between 25 degrees and 85 degrees with respect to the first section of the handle assembly.

13. The medical device of claim 11, wherein the second section of the handle assembly form an angle between 40 degrees and 70 degrees with respect to the first section of the handle assembly.

14. A medical device for stone management, comprising:
- a multi-lumen catheter comprising a proximal end, a distal end, and an inner lumen and an outer lumen at least partially surrounding the first lumen;
- a handle assembly interconnected with the proximal end of the catheter, the handle assembly comprising a body defining an interior cavity, a first section and a second section;
- an interior passageway disposed within the interior cavity; the interior passageway in fluid communication with the outer lumen of the catheter and having a first end and a second end;
- a valve assembly positioned within the interior passageway, the valve assembly moveable between a first position and a second position;
- an actuator assembly engaged with the valve assembly; and
- a vacuum port positioned on the second section of the handle assembly and in fluid communication with the interior passageway;
- wherein the second section of the handle assembly forms an angle with respect to the first section of the handle assembly,
- wherein the actuator allows for incremental movement of the valve assembly between the first position to the second position, and
- wherein the second end of the interior passageway is adjacent to the vacuum port.

15. The medical device of claim 14, further comprising a hub positioned within the interior cavity of the handle assembly, the hub comprising a first port, a second port, third port, and a central passage.

16. The medical device of claim 15, wherein a proximal end of the catheter is in contact with the central passage.

17. The medical device of claim 15, wherein the first end of the interior passageway is in communication with the first port of the hub.

18. The medical device of claim 15, wherein the handle assembly further comprises a connector in communication with the second port of the hub.

19. The medical device of claim 15, wherein the handle assembly further comprises an irrigation port in communication with the third port of the hub.

20. A medical device for stone management, comprising:
- a multi-lumen catheter comprising a proximal end, a distal end, an inner lumen and an outer lumen at least partially surrounding the first lumen;
- a handle assembly interconnected with the proximal end of the catheter, the handle assembly comprising a body defining an interior cavity, a first section and a second section;
- an interior passageway disposed within the interior cavity, the interior passageway in fluid communication with the outer lumen of the catheter and having a first end and a second end;
- a hub positioned within the interior cavity of the handle assembly and in communication with the interior passageway, the hub comprising a first port, a second port, third port, and a central passage;
- a valve assembly positioned within the interior passageway, the valve assembly moveable between a first position and a second position;
- an actuator assembly engaged with the valve assembly; and
- a vacuum port positioned on the second section of the handle assembly and in fluid communication with the interior passageway;
- wherein the second section of the handle assembly forms an angle with respect to the first section of the handle assembly,
- wherein the actuator allows for incremental movement of the valve assembly between the first position to the second position, and
- wherein the second end of the interior passageway is adjacent to the vacuum port.

* * * * *